United States Patent
Dudnyk et al.

(10) Patent No.: US 8,697,112 B2
(45) Date of Patent: Apr. 15, 2014

(54) METHOD FOR TREATING A SURFACE WITH A COATING COMPRISING A MICROENCAPSULATED THERAPEUTIC AGENT AND DEVICE WITH TREATED SURFACE

(75) Inventors: Vyacheslav Dudnyk, Mississauga (CA); Valerio DiTizio, Toronto (CA)

(73) Assignee: Covalon Technologies, Mississauga (CA)

( * ) Notice: Subject to any disclaimer, the term of this patent is extended or adjusted under 35 U.S.C. 154(b) by 0 days.

(21) Appl. No.: 13/543,337

(22) Filed: Jul. 6, 2012

(65) Prior Publication Data

US 2013/0039953 A1   Feb. 14, 2013

Related U.S. Application Data

(60) Provisional application No. 61/505,748, filed on Jul. 8, 2011.

(51) Int. Cl.
*A61F 2/02* (2006.01)
*A01N 25/08* (2006.01)
*A61K 9/14* (2006.01)
*A61K 9/50* (2006.01)

(52) U.S. Cl.
USPC ........... 424/425; 424/409; 424/486; 424/487; 424/501

(58) Field of Classification Search
None
See application file for complete search history.

(56) References Cited

U.S. PATENT DOCUMENTS

| 6,808,738 B2 | 10/2004 | DiCosmo et al. |
| 2009/0035388 A1 | 2/2009 | Dudnik et al. |
| 2011/0212152 A1 | 9/2011 | Ditizio et al. |

FOREIGN PATENT DOCUMENTS

| WO | 02070022 | * | 9/2002 |
| WO | 02070022 A2 | | 9/2002 |
| WO | 2011/038483 | * | 4/2011 |
| WO | 2011038483 A1 | | 4/2011 |

OTHER PUBLICATIONS

International Search Report and Written Opinion mailed Oct. 17, 2012, in related PCT Patent Application No. PCT/CA2012/000629.
Cortes-Cortes, P. et al., "Magnetic behaviour and antibacterial activity of iron (III) complexes," Journal of the Chilean Chemical Society, 2008, vol. 53, No. 2, pp. 1527-1532.
Domenico, P., "Enhancement of Bismuth Antibacterial Activity with Lipophilic Thiol Chelators," Antimicrobial Agents and Chemotheraphy, 1997, vol. 41, No. 8, pp. 1697-1703.
Morrier, J.J. et al., "Antimicrobial activity of amalgams, alloys and their elements and phases," 1998, vol. 14, No. 2, pp. 150-157 (Abstract Only).
Pissuwan, D. et al., "Functionalized gold nanoparticles for controlling pathogenic bacteria," Trends in Biotechnology, 2010, vol. 28, No. 4, pp. 207-213 (Abstract Only).

(Continued)

*Primary Examiner* — Carlos Azpuru

(57) ABSTRACT

A method for treating a surface with a therapeutic agent is disclosed. The method comprises precipitating a therapeutic agent from a hydrophilic polymeric base layer with which the therapeutic agent has been complexed, to form a layer comprising microparticles of the therapeutic agent on the hydrophilic polymeric base layer, the hydrophilic polymeric base layer being grafted to the surface. Devices comprising a surface having a hydrophilic polymeric base layer comprising a hydrophilic polymer grafted to the surface and a layer comprising microparticles of a therapeutic agent disposed on and complexed with the hydrophilic polymeric base layer are also disclosed.

11 Claims, 3 Drawing Sheets

(56) References Cited

OTHER PUBLICATIONS

Varkey, A.J., "Antibacterial properties of some metals and alloys in combating coliforms in contaminated water," Scientific Research and Essays, 2010, vol. 5, No. 24, pp. 3834-3839.

Yasuyuki, M. et al. "Antibacterial properties of nine pure metals: a laboratory study using *Staphylococcus aureus* and *Escherichia coli*", Biofouling: The Journal of Bioadhesion and Biofilm Research, 2010, vol. 26, No. 7, pp. 851-858 (Abstract Only).

\* cited by examiner

METHOD FOR TREATING A SURFACE WITH A COATING COMPRISING A MICROENCAPSULATED THERAPEUTIC AGENT AND DEVICE WITH TREATED SURFACE

CROSS-REFERENCE TO RELATED APPLICATIONS

The present application claims priority from U.S. Provisional Patent Application No. 61/505,748 filed Jul. 8, 2011, the contents of which are hereby incorporated by reference.

FIELD OF THE INVENTION

The present invention relates to methods for treating a surface with a coating comprising a therapeutic agent and to devices, including implantable medical devices, having a surface treated in accordance with such methods.

BACKGROUND

In the medical field, devices are often implanted into the body for therapeutic purposes. Therapeutic effects of such devices tend to be realised by physical effects. For example, catheters of many types are often inserted into blood vessels or various body cavities for the purpose of allowing the entrance or exit of fluids. As examples, Foley catheters allow for drainage of urine, while intravenous catheters facilitate the injection of various therapeutic agents into the blood stream, while also enabling blood sampling. Other catheter types, such as coronary or angioplasty catheters, act by physically changing the shape of the blood vessel. Other examples of implantable medical devices include orthopedic implants, which are used to repair or replace native structural tissues, and permanent dental implants.

In addition to the therapeutic effects being realized through physical effects such as those described above, implantable medical devices may also be designed to deliver therapeutic agents at the site of implantation in order to increase the positive effects of the implant treatment.

There exists a need for alternative methods of applying coatings comprising therapeutic agents to surfaces of devices and to provide implantable devices, including medical devices, with such coatings.

SUMMARY OF THE INVENTION

The present invention provides a method for treating a surface with a coating that comprises a therapeutic agent. The method involves precipitating the therapeutic agent from a hydrophilic polymeric base layer that has been grafted to the surface, thus forming a layer comprising microparticles, for example microcrystals, of the therapeutic agent on the hydrophilic polymeric base layer. Prior to precipitating, the therapeutic agent has been complexed with the hydrophilic polymeric base layer. If desired, a hydrophobic polymer may be layered over the layer comprising the microparticles of the therapeutic agent to form a top layer of the coating.

Thus the coating, once formed in accordance with the method exemplary of an embodiment of the invention, includes a hydrophilic polymeric base layer grafted to the surface, a layer comprising microparticles of the therapeutic agent precipitated from the hydrophilic polymeric base layer, and optionally, a hydrophobic polymeric top layer.

In one aspect, the present invention provides a method for treating a surface, comprising: precipitating a therapeutic agent from a hydrophilic polymeric base layer with which the therapeutic agent has been complexed, to form a layer comprising microparticles of the therapeutic agent on the hydrophilic polymeric base layer, the hydrophilic polymeric base layer being grafted to the surface.

The method may further comprise, prior to precipitating, complexing the therapeutic agent with the hydrophilic polymeric base layer that is grafted to the surface.

In some embodiments of the method, complexing may comprise incubating the hydrophilic polymeric base layer in a concentrated solution comprising the therapeutic agent.

The method may also further comprise, prior to complexing, grafting a hydrophilic polymer to the surface to form the hydrophilic polymeric base layer on the surface.

The hydrophilic polymer may comprise, in some embodiments, hydrophilic polyacrylate, polyethylene oxide, polyethylene glycol, polyethyleneimine or polyvinylpyrrolidone, or any mixture thereof, or any copolymer comprising repeating units of two or more thereof.

In other embodiments, the hydrophilic polymer may comprise collagen, cellulose, dextran, chitosan, alginate, pectin or guar gum.

The method may further comprise applying a solution comprising a hydrophobic polymer on the layer comprising microparticles of the therapeutic agent to form a hydrophobic polymeric top layer.

The hydrophobic polymer may comprise poly(butyl methacrylate), poly(decyl acrylate), polylauryl acrylate, polystyrene, poly(dimethylsiloxane) or poly(vinyl butyral), or any mixture thereof.

In some embodiments, grafting may comprise: immersing the surface in an alcoholic solution of a photoinitiator to adhere the photoinitiator to the surface; incubating the surface with the photoinitiator adhered thereto in an aqueous solution of a monomer capable of free radical polymerization; and irradiating the incubating surface with ultraviolet light to form the hydrophilic polymeric base layer grafted to the surface.

The photoinitiator may comprise a perester, an α-hydroxyketone, a diphenyl ketone, a benzil ketal or a benzoin, or any derivative thereof or any mixture thereof. In one embodiment, the photoinitiator comprises a mixture of tert-butyl peroxybenzoate and benzophenone.

The monomer may comprise acrylic acid, methacrylic acid, methyl acrylate, 2-carboxyethyl acrylate, 4-vinylbenzoic acid, itaconic acid, acrylamide, 4-ethenyl-benzenesulfonic acid, vinyl acetate, dimethylaminoethyl acrylate, ethylene glycol methacrylate, 2-methacryloyloxyethyl phosphorylcholine or N-vinyl pyrrolidone, or any mixture thereof. In one embodiment, the monomer comprises a mixture of acrylic acid and methyl acrylate.

The aqueous monomer solution may comprise an additional photoinitiator.

The method may further comprise treating the hydrophilic polymeric base layer with an aqueous base solution prior to the complexing.

The aqueous base solution may have a pH of 8 or higher.

In some embodiments, the aqueous base solution may comprise disodium tetraborate, sodium carbonate, ammonium hydroxide, calcium hydroxide, sodium hydroxide or tris(hydroxymethyl)aminomethane, or any mixture thereof. In one embodiment, the aqueous base solution comprises tris(hydroxymethyl)aminomethane.

The therapeutic agent may comprise a drug, a sclerosing agent, an antimicrobial agent, a nutrient, a supplement, a (poly)peptide or a (poly)nucleic acid.

In one embodiment, the therapeutic agent comprises a sclerosing agent.

The sclerosing agent may comprise silver nitrate, bleomycin, doxycycline, iodine, or magnesium silicate, or any mixture thereof. In one embodiment, the sclerosing agent comprises silver nitrate.

In one embodiment, the therapeutic agent comprises an antimicrobial agent.

The antimicrobial agent may comprise silver acetate, silver benzoate, silver carbonate, silver citrate, silver chloride, silver iodate, silver iodide, silver lactate, silver laurate, silver nitrate, silver oxide, silver palmitate, silver phosphate, silver salicylate, silver sulfadiazine, silver thiosulfate, silver zeolite or a silver complex, or any mixture thereof. In one embodiment, the antimicrobial agent comprises silver acetate. The silver acetate may be photostabilized.

The antimicrobial agent may be based on mercury, copper, iron, lead, zinc, bismuth, gold or aluminium.

In some embodiments of the method, the precipitating may be effected by heating the surface, exposing the surface to a stream of forced gas or immersing the surface in a secondary precipitation-inducing solution, or any combination thereof. In one embodiment, the precipitating is effected by exposing the surface to a stream of nitrogen gas.

The surface may be formed from a natural polymer, a synthetic polymer, a metal, a metal alloy, a metal oxide, a quartz, a ceramic, a glass, a glass-ceramic, a silicate material or a carbon material, or any combination thereof.

In another aspect of the present invention, there is provided a method for treating a surface of a device, comprising: immersing the surface in an alcoholic solution of a photoinitiator to adhere the photoinitiator to the surface; incubating the surface with the photoinitiator adhered thereto in an aqueous solution of a monomer capable of free radical polymerization; irradiating the incubating surface with ultraviolet light to form a hydrophilic polymeric base layer grafted to the surface; incubating the hydrophilic polymeric base layer in a saturated or near saturated solution comprising the therapeutic agent, thereby complexing the therapeutic agent with the hydrophilic polymeric base layer; and forming a layer comprising microparticles of the therapeutic agent on the hydrophilic polymeric base layer by precipitating the therapeutic agent that is complexed therewith.

The method may further comprise treating the surface grafted with the hydrophilic polymeric base layer with an aqueous base solution prior to the incubating the hydrophilic polymeric base layer.

The method may also further comprise applying a solution comprising a hydrophobic polymer on the layer comprising microparticles of the therapeutic agent to form a hydrophobic polymeric top layer.

The therapeutic agent may comprise a silver-based antimicrobial agent.

In another aspect of the present invention, there is provided an implantable medical device prepared according to a method of the invention.

In another aspect of the present invention, there is provided a device comprising: a surface; a hydrophilic polymeric base layer comprising a hydrophilic polymer grafted to the surface; and a layer comprising microparticles of a therapeutic agent disposed on and complexed with the hydrophilic polymeric base layer.

The device may be a medical device, including for example an implantable medical device.

The implantable medical device may comprise a dressing, a pin, a clip, a catheter, a stent, an implant, a tubing, a rod, a prosthesis, a screw, a plate, a stent, an endotracheal tube, a heart valve, a dental implant, or a drug delivery device.

The device may be a medical device for inducing pleurodesis, preventing restenosis, or for treating tumors.

In some embodiments, the therapeutic agent comprises silver nitrate.

The microparticles of the therapeutic agent may have dimensions in the range of from about 1 μm to about 500 μm.

The hydrophilic polymeric base layer may have a thickness in the range of about 0.1 μm to about 500 μm.

The layer comprising microparticles of the therapeutic agent may have a thickness in the range of about 10 μm to about 500 μm.

The device may further comprise a hydrophobic polymeric top layer on the layer of the therapeutic device. The hydrophobic polymeric top layer may have a thickness in the range of about 1 μm to about 500 μm.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
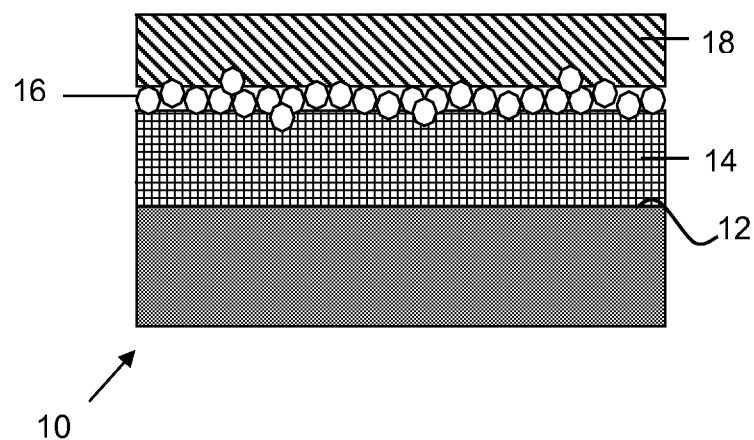
FIG. 1 is a schematic diagram of a surface of an implantable medical device that has been treated with a coating comprising a therapeutic agent prepared in accordance with an embodiment of the invention.

There is provided a method of treating a surface. The surface is a surface of a device and the method results in provision of a coating on the surface. The coating comprises a layer that includes microparticles of a therapeutic agent. The method involves precipitating a therapeutic agent from a hydrophilic polymeric base layer, with which the therapeutic agent is complexed. Prior to the precipitation, the hydrophilic polymeric base layer is grafted to the surface. The precipitation of the complexed therapeutic layer from the hydrophilic polymeric base layer results in formation of the layer that contains microparticles of the therapeutic agent.

An exemplary embodiment of the method is now described.

The surface is any surface to be treated with the coating comprising the therapeutic agent.

For example, the surface may be a surface of an implantable device or a device that is to come into contact with the body of a subject. Thus, the device may be an implantable device such as a medical device, including implantable medical devices which are manufactured to replace a missing biological structure, support a damaged biological structure, enhance an existing biological structure, or deliver a therapeutic agent, as with a drug delivery device. Implantable medical devices include, but are not limited to, dressings, pins, clips, catheters, stents, implants, tubings, rods, prostheses, screws, plates, stents, endotracheal tubes, heart valves, dental implants and the like. Alternatively, the surface may be a surface of a device designed to be in contact with the body of a subject, for example metal body piercing materials such as studs and the like.

The surface is formed from a material that forms at least an outer layer of the device. The surface may be formed from an organic or inorganic material. Suitable organic or inorganic materials include polymers, including natural or synthetic polymers, metals, metal alloys, metal oxides, quartz, ceramics, glasses, glass-ceramics, silicate materials, carbon materials such as graphite, or any combination thereof.

Examples of suitable natural or synthetic polymers that may form the surface include polyurethanes, polyamides, polyimides, polycarbonates, polyesters, polyvinylchlorides, polyethers, polyorganosiloxanes, polysulfones, polytetrafluoroethylenes, polysiloxanes (silicones), polyethylenes, polypropylenes, polyether ether ketones, polystyrenes, polyacrylates, acrylonitrile butadiene styrene (ABS) polymers, latex, synthetic rubber and the like.

Examples of suitable metals include metals such as titanium, palladium, platinum, gold, silver, rhodium, zirconium and iridium, and also include metal alloys such as titanium alloys (containing one or more of chromium, nickel, aluminum, vanadium, cobalt, for example but not limited to, $TiAl_6V_4$, $TiAlFe_{2.5}$), stainless steel (such as implant grade material, e.g. V2A, V4A, martensitic steel and austenitic steel, for example, 316L and 316LVM), cobalt alloys, gold alloys, tungsten alloys, molybdenum alloys, chromium alloys and cobalt-chromium alloys.

In the method, the hydrophilic polymer is grafted to the surface to form a hydrophilic polymeric base layer.

The hydrophilic polymer may be a polymer that is generally soluble in water or polar solvent. The hydrophilic polymer comprises at least one or more types of hydrophilic groups, either in the main polymer chain or attached as a pendant group.

Examples of synthetic hydrophilic polymers include, but are not limited to, hydrophilic polyacrylates such as polyacrylic acid, polyacrylamide, polystyrene sulfonic acid, or polyvinyl acetate, other hydrophilic polymers such as polyethylene oxide, polyethylene glycol, polyethyleneimine, or polyvinylpyrrolidone, or any mixture thereof, as well as any copolymer comprising repeating units of any of the aforementioned hydrophilic polymers. Examples of suitable natural hydrophilic polymers include collagen, cellulose, dextran, chitosan, alginate, pectin or guar gum.

Suitable hydrophilic polymers may also be capable of absorbing large quantities of water, for example, by swelling. Without being limited to any particular theory, since the therapeutic agent is likely to be water-soluble, the more water the hydrophilic polymer can absorb, the greater the quantity of the agent that can be loaded onto the surface.

The grafting results in attachment of the hydrophilic polymer to the surface, and the grafting reaction and form of attachment will vary depending on the various functional groups included in the hydrophilic polymer. Thus, the grafting may be achieved using standard techniques, including formation of a covalent bond, a coordinate bond, and/or hydrogen bonding between complementary reactive groups on the hydrophilic polymer and the surface on which the hydrophilic polymer is to be grafted. Exemplary suitable techniques are disclosed in U.S. Pat. No. 6,808,738 to DiTizio and DiCosmo, WO02/070022 to DiTizio and DiCosmo, and U.S. patent application Ser. No. 12/982,178 to DiTizio and DiCosmo.

One skilled in the art would readily appreciate that the level of grafting of the hydrophilic polymer to the surface may be controlled by adjustment of reaction parameters such as type of material forming the surface, type of polymer or monomer to be polymerized, concentration of the polymer or monomer, temperature, duration of reaction and other parameters involved in determining the reaction conditions. Suitable reaction conditions can be readily determined using routine laboratory techniques.

The extent of grafting of the hydrophilic polymer to the surface may provide a substantially uniform layer. To maximize the loading of the therapeutic agent onto the surface, the hydrophilic polymeric base layer may have a thickness in the range of about 0.1 μm to about 500 μm, about 1 μm to about 200 μm, or about 10 μm to about 100 μm.

As will be appreciated, grafting of the hydrophilic polymer to the surface can occur via a grafting-to or a grafting-from process.

In some cases, depending on the nature of the material forming the surface, activation of the surface prior to addition of the polymer for grafting or addition of a monomer for polymerizing and grafting may facilitate the reaction between the surface and the polymer. The activation of the surface may be achieved in any manner known to those skilled in the art, for example, oxidation.

In a grafting-to process, a pre-formed polymer is attached to the surface via a grafting reaction. A solution containing the hydrophilic polymer is added to the surface under suitable conditions that allow for reaction between the surface and the reactive groups in the hydrophilic polymer, to form the hydrophilic polymeric base layer grafted to the surface. The binding of the polymer to the surface may be induced through heat, light, or other input of energy.

If desired, the surface may first be activated or pre-treated prior to grafting. For example, if the surface is formed from metal, the surface may be oxidized to more readily react with the pre-formed polymer once added. Other common surface pre-treatments include exposure to corona or plasma discharge, high intensity UV light, gamma radiation, or ozone.

In a grafting-from process, the hydrophilic polymer is synthesized in an in situ polymerization process from a monomer added to the surface. At least one monomer unit may be attached to the surface, allowing for polymerization from the grafted monomer. Alternatively, during an in situ polymerization, a free radical group is generated on the surface causing a reaction between the surface and a monomer or a group within the nascent polymer.

In one particular example of the grafting-from process, a hydrophilic polymeric base layer is grafted to the surface in the following manner. The surface is immersed in an alcoholic solution of a photoinitiator to adhere the photoinitiator to the surface; the surface with the adhered photoinitiator is subsequently incubated in an aqueous solution containing a monomer capable of free radical polymerization; and the incubating surface is irradiated with ultraviolet (UV) light to form the hydrophilic polymeric base layer, which is grafted to the surface through covalent bonds between the hydrophilic polymer and the surface.

A suitable photoinitiator is adhered to the surface in any manner known to those skilled in the art. For example, the photoinitiator may be coated to the surface by immersing the surface in an alcoholic solution of the photoinitiator at ambient temperature. Isopropyl alcohol is one example of an alcohol that may be used.

Suitable photoinitiators include, but are not limited to, peresters, α-hydroxyketones, diphenyl ketones, benzil ketals, benzoins, their derivatives or mixtures thereof. Specifically, suitable photoinitiators may be selected from 2,2-dimethoxy-2-phenyl-acetophenone (DPA), p-benzoyl tert-butylperbenzoate (BPB), benzophenone (BP), tert-butyl peroxybenzoate (TBP) or mixtures thereof. In one example, the photoinitiator is a mixture of TBP and BP.

The surface coated with the photoinitiator is incubated in an aqueous solution of a monomer capable of free radical polymerization, in manners known to those skilled in the art. For example, the photoinitiator coated surface may be immersed in the aqueous monomer solution, which has been purged with an inert gas such as nitrogen for a sufficient period of time to remove oxygen from the solution.

Suitable monomers can be any hydrophilic monomers that are capable of free-radical-mediated polymerization under UV light. They include, but are not limited to, acrylic acid, methacrylic acid, methyl acrylate, 2-carboxyethyl acrylate, 4-vinylbenzoic acid, itaconic acid, acrylamide, 4-ethenylbenzenesulfonic acid, vinyl acetate, dimethylaminoethyl acrylate, ethylene glycol methacrylate, 2-methacryloyloxyethyl phosphorylcholine, N-vinyl pyrrolidone, or mixtures thereof. In one embodiment, the monomer is a mixture of acrylic acid and methyl acrylate.

The aqueous monomer solution may include additional photoinitiators to increase the efficiency of the grafting reaction. The solution may contain the additional photoinitiator in the range from about 0.1 µg/mL to about 100 µg/mL, for example from about 1 to about 10 µg/mL.

A suitable wavelength for the UV radiation can be in the range from about 180 nm to about 450 nm, from about 240 to about 400 nm, or from about 350 nm.

Once the hydrophilic polymeric base layer is grafted to the surface, the therapeutic agent is complexed with the hydrophilic polymeric base layer.

The therapeutic agent is any agent that provides a therapeutic effect when provided in the coating on a device implanted in or in contact with the body of a subject, including curative, palliative, prophylactic or nutritional effect.

Suitable therapeutic agents include, but are not limited to, any class of pharmaceutical compound, drug (e.g. ibuprofen, tamoxifen, rapamycin), small molecule (e.g. salicylic acid, resveratrol, cationic metalloporphyrins), sclerosing agent (e.g. silver nitrate, bleomycin, doxycycline), antimicrobial agent (e.g. silver acetate, chlorhexidine, miconazole), nutrient (e.g. glucose, sodium lactate, magnesium sulphate), supplement (e.g. glucosamine, ascorbic acid, potassium iodide), (poly)peptides (e.g. fibroblast growth factor, insulin/glucagon, substance P), and (poly)nucleic acids (e.g. small interfering RNA, anti-sense RNA/DNA, locked nucleic acids).

For example, the therapeutic agent may be an antimicrobial agent, which includes, but is not limited to, silver and its salts and oxides, such as silver acetate, silver benzoate, silver carbonate, silver citrate, silver chloride, silver iodate, silver iodide, silver lactate, silver laurate, silver nitrate, silver oxide, silver palmitate, silver phosphate, silver salicylate, silver sulfadiazine, silver thiosulfate, silver zeolite, or other silver complexes, or mixtures thereof. The silver antimicrobial agent may be further photostabilized to deter photo-induced discoloration using standard techniques known to those skilled in the art. For example, the silver agent may be photostabilized with DL-pyroglutamic acid and Brilliant Green as is disclosed, for example, in U.S. Patent Publication No. 2009/0035388 to Dudnik et al. Other non-silver containing antimicrobial agents may also be used, for example, any metal with antimicrobial properties, including for example mercury, copper, iron, lead, zinc, bismuth, gold or aluminium.

Complexing is achieved, for example, by incubating the hydrophilic polymeric base layer in a solution containing the therapeutic agent. At least a portion, group or moiety of the therapeutic agent will bind to at least a portion, group or moiety of the hydrophilic polymeric base layer in order to form a complex. Binding between the therapeutic agent and the grafted hydrophilic polymer may involve covalent, ionic, chelation, coordination, hydrogen bonding, electrostatic, ring stacking or pi-pi interactions.

For example, the surface grafted with the hydrophilic polymeric base layer is incubated in an aqueous solution comprising the therapeutic agent for a sufficient time and under conditions that allow at least a portion of the therapeutic agent to be complexed with at least a portion of the hydrophilic polymer contained in the hydrophilic polymeric base layer.

In some instances, the surface grafted with the hydrophilic polymeric base layer may be immersed in an aqueous solution of the therapeutic agent for about 30 seconds at ambient temperature, and in other instances, for about 1 hour or more.

In addition to, or alternative to aqueous solutions, the solution may include any polar solvents that can cause the hydrophilic polymer to swell while solubilising the therapeutic agent. For example, short-chain alcohols may be used as a solvent.

The solution is a concentrated solution of the therapeutic agent. A concentrated solution is a solution containing sufficient concentration of the therapeutic agent to allow for complexation and subsequent precipitation of the therapeutic agent to form microparticles. Depending on the desired loading level of the therapeutic agent, the concentration of the therapeutic agent in the solution may be adjusted accordingly. As will be appreciated, the higher the concentration, the higher the loading of the therapeutic agent that may result. For example, the solution may be saturated or near saturated with the therapeutic agent such that a high loading of the therapeutic agent on the surface may be achieved.

A skilled person can readily prepare a concentrated solution of the therapeutic agent using routine laboratory experimentation, including preparation of a saturated or near saturated solution of the therapeutic agent. For example, a saturated solution may be prepared by dissolving the therapeutic agent in the appropriate solvent at ambient temperature until no more therapeutic agent can be dissolved and any additional amount appears as a precipitate.

Using a concentrated solution of the therapeutic agent allows for inclusion of a greater amount of the therapeutic agent in the coating and may facilitate microcrystal formation upon precipitation of the complexed therapeutic agent. It is also believed that the complexation between the therapeutic agent and the hydrophilic polymer may lead the precipitated therapeutic agent to form microcrystals.

Optionally, the hydrophilic polymeric base layer may be pre-treated prior to complexing of the therapeutic agent, in order to facilitate the complexing. For example, prior to incubating with the hydrophilic polymeric base layer with the therapeutic agent, the hydrophilic polymeric base layer grafted on the surface may be treated with an aqueous base solution having a pH equal to or greater than about 8.0 so that the surface becomes negatively charged. The negatively charged surface may then be incubated in the solution comprising the therapeutic agent. Without being limited to any particular theory, the negatively charged surface may strengthen the complexation between the hydrophilic polymer contained in the hydrophilic polymeric base layer and the therapeutic agent via chemical bonding such as ionic bonding.

Suitable aqueous bases for use include, but are not limited to, disodium tetraborate (borate buffer), sodium carbonate, hydroxides such as ammonium hydroxide, calcium hydroxide or sodium hydroxide, Tris or TRIZMA® (tris(hydroxymethyl)aminomethane), or any mixture thereof.

For example, a surface grafted with a hydrophilic polymeric base layer is treated with an aqueous base solution of 50 mM TRIZMA®, for about 10 minutes at ambient temperature. The negatively charged surface so generated is subsequently incubated briefly at ambient temperature in a concentrated solution of a therapeutic agent, for example, a silver salt.

As a further option, the surface may be coated with a cationic hydrophilic polymer. The positively charged surface may then be incubated in an aqueous solution comprising a therapeutic agent carrying a negative charge such that the complexation between the hydrophilic polymer and the therapeutic agent may be achieved through a chemical bonding such as ionic bonding.

Once complexed, the therapeutic agent is precipitated to form a layer comprising microparticles of the therapeutic agent on the hydrophilic polymeric base layer grafted to the surface.

Precipitation of the therapeutic agent may be effected by a physical or chemical means, or both, for example, by any suitable routine laboratory techniques known to those skilled in the art. As an example, to initiate precipitation of the therapeutic agent, the coated surface may be heated, exposed to a stream of forced gas such as nitrogen gas, lyophilized, or immersed in a secondary precipitation-inducing solution. A combination of known laboratory precipitation and crystallization techniques may also be used.

The resulting layer comprises the precipitated therapeutic agent. At least a portion of the precipitated therapeutic agent is in the form of microparticles, which may comprise amorphous particles, microcrystals, or both. In some embodiments, at least a portion of the microparticles are microcrystals, but the layer may also include amorphous or non-crystalline precipitated therapeutic agent, or may even include some crystals that are larger than microcrystals.

Thus, the extent of crystallization of the therapeutic agent contained within the layer may vary, depending on the conditions used for precipitation, the nature of the solvent used, the concentration and nature of the therapeutic agent and other factors, as will be appreciated by a person of ordinary skill in the art.

The term microparticle refers to a particle of the therapeutic agent that is not in solution and that has dimensions in the order of micrometers. As indicated above, a microparticle may be disordered (amorphous) or ordered (microcrystal), or may be partially disordered with regions that are ordered as a microcrystal. Similarly, a microcrystal is a crystal having dimensions in the order of micrometers. For example, the microparticle or microcrystal may have dimensions in the range of about 1 µm to about 500 µm, or from about 10 µm to about 150 µm. The dimensions of the microparticle or microcrystal may be determined by standard laboratory techniques known to a skilled person, such as optical microscopy with phase contrast lenses.

The size of the microparticles of therapeutic agent thus obtained may be measured, for example, using optical microscopy techniques with phase contrast lenses. As will be appreciated, the higher the loading of the therapeutic agent onto the surface, the larger the size of the microparticles may become.

The degree of the uniformity of the microparticles in terms of size and in terms of order may also increase with a higher loading of the therapeutic agent. Thus, the size distribution of the microparticles may be fairly uniform or may vary in size, and the microparticles may be microcrystals, disordered precipitate or a combination thereof, depending on the precipitation conditions used and the extent of crystallization of the therapeutic agent upon precipitation.

The layer comprising microparticles of the therapeutic agent may be continuous, meaning that the layer substantially covers the hydrophilic polymeric base layer on the surface, without gaps or holes, or may be discontinuous, having some regions of the surface that may not be covered by the layer comprising microparticles of the therapeutic agent, or having some gaps or holes in the layer.

The layer may be generally uniform in terms of thickness, but there may be a variation including a gradient in thickness, for example due to the effects of gravity during the incubating and/or precipitating steps. The layer comprising microparticles of the therapeutic agent may have a thickness in the range from about 10 µm to about 500 µm, for example about 20 µm to about 200 µm.

The amount of the therapeutic agent that can be coated onto the surface may be determined by using any standard quantification methods, such as extracting the coated surface with a suitable solvent followed by measuring the concentration of the therapeutic agent via a standard method, e.g. high-performance liquid chromatography (HPLC).

In order to further control the release of the therapeutic agent from the coating when the device is implanted in or in contact with a subject's body, the method may optionally further comprise applying a solution comprising a hydrophobic polymer over the layer comprising the microparticles of the therapeutic agent so that a hydrophobic polymeric top layer is formed.

Without being limited to any particular theory, the therapeutic agent may be released as a result of diffusion of the agent through the hydrophobic polymeric top layer and/or slow erosion of the hydrophobic polymeric top layer. The hydrophobic polymeric top layer may therefore be porous.

The hydrophobic polymer is a polymer that tends to have minimal solubility in water or a polar solvent. The hydrophobic polymer comprises at least one or more types of hydrophobic groups, either in the main polymer chain or attached as a pendant group.

It will be appreciated that the hydrophobic polymeric top layer should be sufficiently hydrophobic to act as a barrier to regulate release of the therapeutic agent while still being able to interact to some extent with the underlying hydrophilic polymeric base layer in order to form a substantially uniform top coating that adheres to the layer comprising the microparticles of the therapeutic agent.

Suitable hydrophobic polymers include, but are not limited to, poly(butyl methacrylate), poly(decyl acrylate), polylauryl acrylate, polystyrene, poly(dimethylsiloxane), poly(vinyl butyral), and any mixture thereof.

Formation of the hydrophobic polymeric top layer may be accomplished by immersing the treated surface having the layer of the precipitated therapeutic agent in a solution comprising the hydrophobic polymer for a time sufficient for the hydrophobic polymeric top layer to form a coating over the layer comprising microparticles of the therapeutic agent. The top coating thus formed may be substantially uniform and may have a thickness in the range from about 1 µm to about 500 µm, such as about 10 µm to about 100 µm.

As will be appreciated, the hydrophobic polymer is preferably dissolved in a solvent that does not dissolve the therapeutic agent during the application process such that the therapeutic agent layer is not lost. For example, the solvent may be ethanol, ethyl acetate, chloroform, or a non-polar solvent that does not dissolve the therapeutic agent and/or damage the surface.

The methods described herein may be used to apply coatings comprising therapeutic agents to surfaces of medical devices, for example, implantable medical devices. The coated devices may be used to deliver the therapeutic agent, while performing their standard function or they may be designed specifically to carry and deliver the therapeutic agent. Specific applications may include the induction of pleurodesis by a silver nitrate-coated chest drain, the prevention of restenosis by sirolimus-coated coronary stents, or the treatment of tumours by doxycyline-coated implants. Other applications and uses of the methods are also possible as can be understood by those skilled in the art.

Thus, there is provided a device having a coating comprising a layer comprising microparticles of a therapeutic agent.

Referring to FIG. 1, device 10 has a surface 12.

Device 10 may be a medical device, including an implantable medical device. Implantable medical devices include devices manufactured to replace a missing biological structure, support a damaged biological structure, enhance an existing biological structure, or deliver a specific therapeutic agent. Implantable medical devices include, but are not limited to, dressings, pins, clips, catheters, stents, implants, tubings, rods, prostheses, screws, plates, stents, endotracheal tubes, heart valves and dental implants.

Alternatively, device 10 may be a device designed for implantation in or in contact with a subject's body, for example metal body piercing materials such as studs and the like.

Surface 12 is composed of an organic or inorganic material, including materials such as polymers including natural or synthetic polymers, metals, metal alloys, metal oxides, quartz, ceramics, glasses, glass-ceramics, silicate materials, carbon materials such as graphite, or any combination thereof, including those described in the method above.

Layered on surface 12 is a hydrophilic polymeric base layer 14, which comprises a hydrophilic polymer grafted to the surface 12. The hydrophilic polymer may be any synthetic or natural hydrophilic polymer, and is grafted to surface 12 via covalent bonding, coordinative bonding and/or hydrogen bonding between complementary reactive groups on the polymer and the surface 12.

A layer 16 comprising microparticles of the therapeutic agent is disposed on and within the hydrophilic polymeric base layer 14. In the depicted embodiment, layer 16 comprises microcrystals, although as indicated above, layer 16 may comprise partially or wholly amorphous microparticles.

The therapeutic agent is any therapeutic agent, including a pharmaceutical compound, a drug, a small molecule, an antimicrobial agent, a nutrient, a supplement, a (poly)peptide, or a (poly)nucleic acid. In one example, the therapeutic agent is an antimicrobial agent such as silver nitrate.

Thus, layer 16 may comprise some amorphous therapeutic agent or some crystals that are larger than microcrystals. As described in the method above, microparticles, including for example microcrystals, of the therapeutic agent may have dimensions in the range of about 1 µm to about 500 µm, or from about 10 µm to about 150 µm. As well, the size distribution of the microcrystals of therapeutic agent in layer 16 may be broad or narrow.

Layer 16 has been precipitated from a complex formed between the therapeutic agent and the hydrophilic polymeric base layer 14.

As described in the method above, layer 16 may be continuous, substantially covering surface 12 of device 10. Alternatively, layer 16 may be discontinuous, having one or more gaps or holes formed in layer 16.

Layer 16 may be of substantially uniform thickness or may vary in thickness. Layer 16 may have a thickness in the range from about 10 µm to about 500 µm, for example about 20 µm to about 200 µm.

Hydrophobic polymeric top layer 18 comprising a hydrophobic polymer is disposed on the layer 16 of precipitated therapeutic agent. As indicated in the method described above, the hydrophobic polymer used to form hydrophobic polymeric top layer 18 may be any hydrophobic polymer, for example poly(butyl methacrylate), poly(decyl acrylate), polylauryl acrylate, polystyrene, poly(dimethylsiloxane), poly(vinyl butyral), and any mixture thereof.

Since the device with the coated surface is to be implanted in or in contact with a subject's body, a skilled person will appreciate that the material forming the surface of the device, the hydrophilic polymer, and the hydrophobic polymer are preferably chosen to be biocompatible.

The described embodiments are susceptible to many modifications of form, arrangement of parts, details and order of operation. The invention, rather, is intended to encompass all such modifications within its scope, as defined by the claims.

The methods and devices described herein are further exemplified by the following non-limiting examples, which are described for the purposes of illustration and are not intended to limit the scope of the invention.

EXAMPLES

Unless otherwise stated, chemicals were obtained from Sigma-Aldrich (Oakville, ON) and used without further purification.

Example 1

Silver Nitrate-Coated Silicone Catheter

Step 1—Hydrophilic Polymeric Base Layer

A silicone catheter (e.g. such as one sold by Degania Medical; Smithfield, R.I.) was soaked in an isopropyl alcohol (98%) solution of photoinitiator containing 400 mM tert-butyl peroxybenzoate (TBP) and 400 mM benzophenone (BP) for 6 minutes at ambient temperature.

The photoinitiator coated silicone catheter was incubated in a 300/50 aqueous monomer solution (300 mM acrylic acid and 50 mM methyl acrylate in deionized water) and the solution was purged with nitrogen for 6 minutes at ambient temperature.

The incubating silicone catheter in the aqueous monomer solution was irradiated with ultraviolet (UV) light at 350 nm for 6 minutes at ambient temperature to initiate polymerization of the monomers on the surface of the silicone catheter and thus to form a hydrophilic polyacrylate (copolymer of polyacrylic acid and poly(methyl acrylate)) base layer, which was grafted to the surface of the silicone catheter.

The polyacrylate grafted silicone catheter was removed from the monomer solution and was washed with 98% IPA for 10 minutes. It was then immersed in 50 mM Trizma® (pH=9.0) at ambient temperature for 10 minutes. This was followed by rinsing in deionized water.

Step 2—Silver Nitrate Layer

The polyacrylate grafted silicone catheter prepared according to the above Step 1 was immersed in an aqueous silver nitrate solution (1.0 g $AgNO_3$/1 ml deionized water, 5883 mM) for 30 seconds at ambient temperature in air. A stream of nitrogen gas was applied through the lumen and over the outer surface of the catheter for 60 seconds to initiate precipitation at ambient temperature.

Step 3—Hydrophobic Polymeric Top Layer

The silver coated silicone catheter prepared in accordance with the above Step 2 was immersed in an ethyl acetate solution of poly(butyl methacrylate) (7.5% w/v) for 30 seconds at ambient temperature in air. The catheter was then removed and dried in air at ambient temperature for at least 16 hours.

The catheter coated in accordance with Example 1 was extracted in an aqueous solution of 1% nitric acid (w/v) and 1% ammonium hydroxide (w/v) for 18 hours followed by measurement of silver nitrate using atomic absorption spectroscopy. Example 1 gave a loading of approximately 100 mg of silver nitrate.

Figure 3:
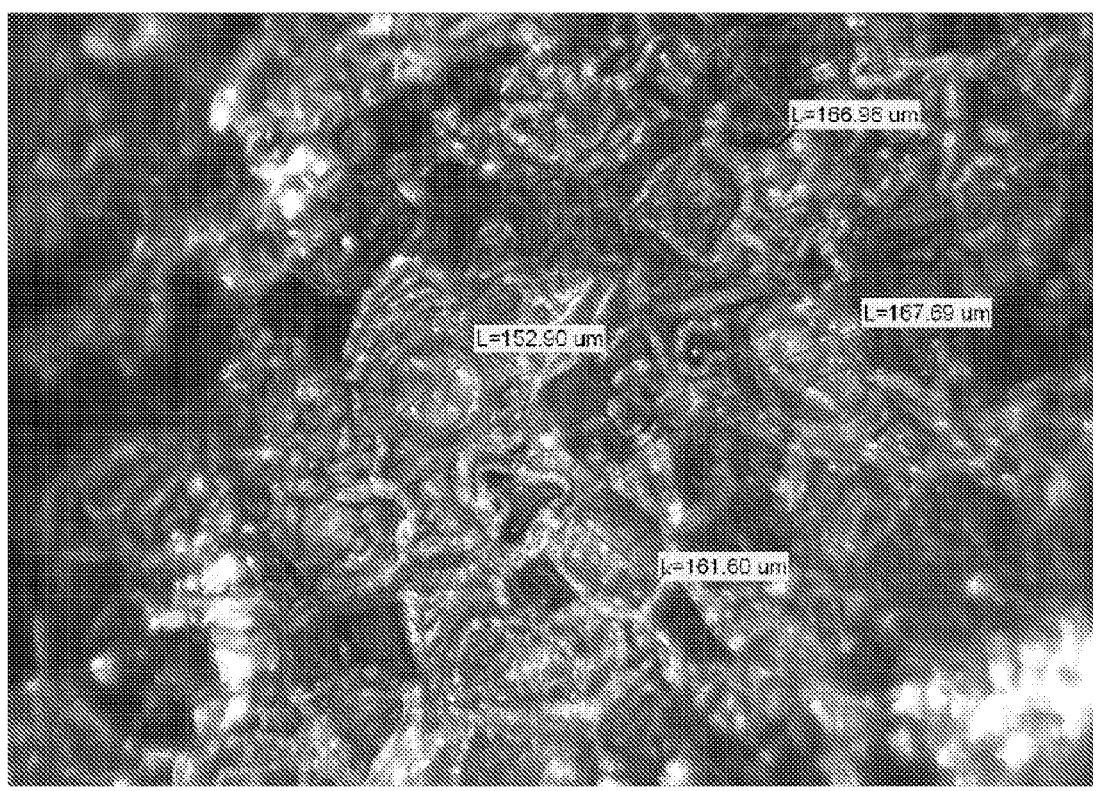

FIG. 3 is a micrograph depicting the surface of the catheter coated with a layer of silver nitrate microcrystals, obtained from Example 1. The micrograph was taken prior to the above Step 3 using an optical microscope equipped with a digital camera (Meiji Techno-MC50T). As shown in FIG. 3, the microcrystals had an average size of about 160 µm.

As can be appreciated, the loading of the silver nitrate may be adjusted by altering the concentration of the aqueous solution containing the silver nitrate. For example, when the concentration was 0.6 g $AgNO_3$/1 ml deionized water, 3530 mM, following Example 1 gave a loading of approximately 60 mg of silver nitrate onto the surface of a catheter.

Figure 2:
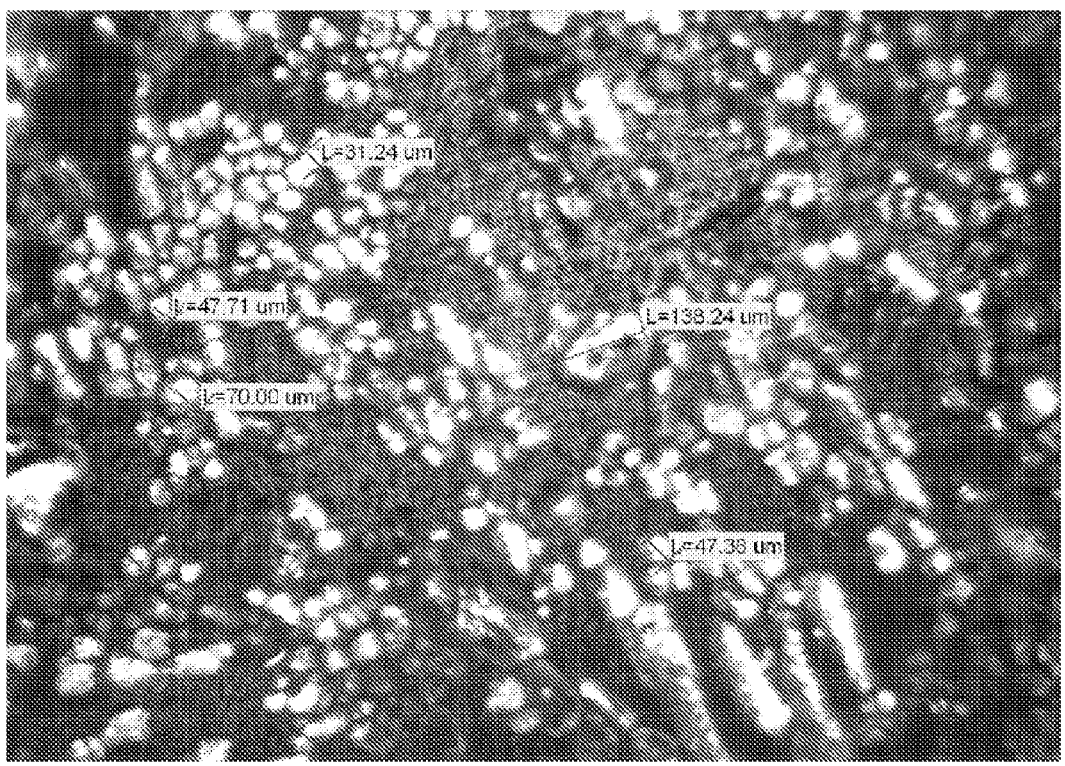
FIGS. 2 and 3 are micrographs of a surface of a catheter coated with a layer comprising silver nitrate microcrystals, in accordance with embodiments of the invention.

FIG. 2 is a micrograph depicting the surface of the catheter which was loaded with about 60 mg of silver nitrate microcrystals in accordance with Example 1. The size of the microcrystals varied from about 30 µm to about 138 µm.

As shown in FIG. 3, a higher loading of the microcrystalline silver nitrate increased the size of the microcrystals, improved the crystallinity of the microcrystals, and the layer covered more area of the hydrophilic base layer.

Example 2

Chlorhexidine-Coated Peripherally Inserted Central (PIC) Catheter

Step 1—Hydrophilic Polymeric Base Layer

A PIC catheter (e.g. such as one 5 Fr double lumen, sold by Bard Access Systems; Salt Lake City, Utah) was soaked in an ethanol (85%) solution of photoinitiator containing 50 mM tert-butyl peroxybenzoate (TBP) and 50 mM benzophenone (BP) for 30 sec at ambient temperature.

The photoinitiator-coated PIC catheter was incubated in a 300/50 aqueous monomer solution (300 mM acrylic acid and 50 mM methyl acrylate in deionized water) and the solution was purged with nitrogen for 6 minutes at ambient temperature.

The incubating PIC catheter in the aqueous monomer solution was irradiated with ultraviolet (UV) light at 350 nm for 3 minutes at ambient temperature to initiate polymerization of the monomers on the surface of the PIC catheter and thus to form a hydrophilic polyacrylate (copolymer of polyacrylic acid and poly(methyl acrylate)) base layer, which was grafted to the surface of the PIC catheter.

The polyacrylate grafted PIC catheter was removed from the monomer solution and was washed in 50 mM Trizma® (pH=9.0) at ambient temperature for 10 minutes. This was followed by rinsing in deionized water.

Step 2—Chlorhexidine Layer

The polyacrylate grafted PIC catheter prepared according to the above Step 1 was immersed in an aqueous chlorhexidine digluconate (CHG) solution (20% CHG w/v) for 30 seconds at ambient temperature in air. A stream of nitrogen gas was applied through the lumens to remove excess solution from the lumens.

Step 3—Chlorhexidine Precipitation on the Surface

The CHG coated PIC catheter prepared in accordance with the above Step 2 was immersed in a 1M NaCl solution for 60 seconds. The CHG transforms to chlorhexidine dihydrochloride and precipitates on the surface. A stream of nitrogen gas was applied through the lumens for 60 seconds to remove excess solution from the lumens. The catheter was then removed and dried in air at ambient temperature for at least 16 hours.

The PIC catheter coated in accordance with Example 2 was extracted in an aqueous solution of 1.5% calcium gluconate (w/v) followed by measurement of chlorhexidine using HPLC. Example 2 gave a loading of approximately 250 µg/cm$^2$ of chlorhexidine.

Conveniently, the methods described herein may produce medical devices with concentrated and homogeneous coatings of therapeutic agents on their surfaces. A robust adhesion of the therapeutic agent to the surface of the medical device may also be achieved. Accordingly, the methods described herein may afford a sustained and controlled release of a therapeutic agent, which is applied to a surface of a medical device, with minimal disruption to the primary function of the device.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

All lists and/or ranges provided herein are intended to include any sub-list and/or narrower range falling within the recited list and/or range.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device comprising:
   a surface;
   a hydrophilic polymeric base layer comprising a hydrophilic polymer grafted to the surface; and
   a layer comprising microparticles of a therapeutic agent disposed on and complexed with the hydrophilic polymeric base layer.

2. The device of claim 1, wherein the device is a medical device.

3. The device of claim 2, wherein the medical device is an implantable medical device.

4. The device of claim 3, wherein the implantable medical device comprises a dressing, a pin, a clip, a catheter, a stent, an implant, a tubing, a rod, a prosthesis, a screw, a plate, a stent, an endotracheal tube, a heart valve, a dental implant, or a drug delivery device.

5. The device of claim 2, wherein the medical device is a device for inducing pleurodesis, preventing restenosis, or for treating tumors.

6. The device of claim 1, wherein the therapeutic agent comprises silver nitrate.

7. The device of claim 1, wherein of the microparticles of the therapeutic agent have dimensions in the range of from about 1 μm to about 500 μm.

8. The device of claim 1, wherein the hydrophilic polymeric base layer has a thickness in the range of about 0.1 μm to about 500 μm.

9. The device of claim 1, wherein the layer comprising microparticles of the therapeutic agent has a thickness in the range of about 10 μm to about 500 μm.

10. The device of claim 1, further comprising a hydrophobic polymeric top layer on the layer of the therapeutic agent.

11. The device of claim 10, wherein the hydrophobic polymeric top layer has a thickness in the range of about 1 μm to about 500 μm.

* * * * *

UNITED STATES PATENT AND TRADEMARK OFFICE
CERTIFICATE OF CORRECTION

| | | |
|---|---|---|
| PATENT NO. | : 8,697,112 B2 | Page 1 of 1 |
| APPLICATION NO. | : 13/543337 | |
| DATED | : April 15, 2014 | |
| INVENTOR(S) | : Vyacheslav Dudnyk et al. | |

It is certified that error appears in the above-identified patent and that said Letters Patent is hereby corrected as shown below:

On the Title Page, Item (54) and in the Specification, Column 1, Lines 1-5, the title should read "METHOD FOR TREATING A SURFACE WITH A COATING COMPRISING A THERAPEUTIC AGENT AND DEVICE WITH TREATED SURFACE"

Signed and Sealed this
First Day of July, 2014

Michelle K. Lee
*Deputy Director of the United States Patent and Trademark Office*